United States Patent [19]

Emodi

[11] 3,961,051

[45] June 1, 1976

[54] JUVENILE HORMONES STABILIZED WITH ACRYLONITRILE U.V. ABSORBERS

[75] Inventor: Alexander Emodi, West Orange, N.J.

[73] Assignee: Hoffmann-La Roche Inc., Nutley, N.J.

[22] Filed: Sept. 20, 1974

[21] Appl. No.: 508,015

Related U.S. Application Data

[63] Continuation-in-part of Ser. No. 323,494, Jan. 15, 1973, abandoned, which is a continuation-in-part of Ser. No. 180,100, Sept. 13, 1971, abandoned.

[52] U.S. Cl............................ 424/174; 424/DIG. 12; 424/278; 424/282
[51] Int. Cl.$^2$............................................. A01N 9/28
[58] Field of Search ..... 424/184, 278, 282, DIG. 12

[56] References Cited
UNITED STATES PATENTS 3,215,724    11/1965    Strobel................................ 424/174

FOREIGN PATENTS OR APPLICATIONS 1,159,137    7/1969    United Kingdom

OTHER PUBLICATIONS

Science, vol. 164, (Apr. 1969), No. 3877, pp. 323–325, Bowers; Wm.

*Primary Examiner*—V. D. Turner
*Attorney, Agent, or Firm*—Samuel L. Welt; Bernard S. Leon; William H. Epstein

[57]    ABSTRACT

A method of stabilizing juvenile hormones against deterioration from air and sunlight by combining the juvenile hormones with substituted acrylonitrile or substituted benzotriazole ultraviolet light absorbers and/or with substituted phenolic anti-oxidants, and the resulting stabilized, insecticide compositions.

12 Claims, No Drawings

JUVENILE HORMONES STABILIZED WITH ACRYLONITRILE U.V. ABSORBERS

RELATED APPLICATIONS

This application is a continuation-in-part of copending U.S. application Ser. No. 323,494 filed Jan. 15, 1973, now abandoned which in turn is a continuation-in-part of U.S. application Ser. No. 180,100 filed Sept. 13, 1971, now abandoned.

BACKGROUND OF THE INVENTION

As used throughout this application, the term "juvenile hormone" comprehends compounds which behave as juvenile hormones, interfering with the hormonal systems of insects, causing their transformation to the imago, their laying of viable eggs and the development of their eggs to be disrupted. These disruptions, characteristic of juvenile hormone activity, prevent affected insects from maturing and proliferating.

Juvenile hormones have been found useful as an active ingredient in many insecticide compositions. Insecticide compositions containing a juvenile hormone have been effective for protecting foodstuffs, feeds, textiles and plants from a wide variety of insect pests. Juvenile hormones do not leave lingering residues in the environment. As a result, insecticide compositions which contain juvenile hormones tend to be less damaging to the environment and, hence, more desirable than other conventional insecticides which contain degradation resistant active ingredients.

In applying juvenile hormones in the field, it has been found that the activity of juvenile hormones has rapidly decreased after their application. For instance, within 24 to 48 hours 1 to 2 days) of their application, certain juvenile hormones become completely degraded and, hence, ineffective against insects with which they subsequently come into contact. This loss of activity of juvenile hormones has not been completely understood. There has been a need, therefore, for an understanding of the causes of this loss of activity and for a means of maintaining the activity of juvenile hormones after their application in the field.

SUMMARY OF THE INVENTION

In accordance with this invention, it has been discovered that the activity of juvenile hormones is deleteriously affected by air and sunlight. Therefore, the prolonged exposure to air and sunlight causes a surprisingly rapid decrease in their potency when applied in the field.

In accordance with this invention, it has been found that by incorporating a substituted phenolic anti-oxidant, and/or an ultraviolet light absorber selected from the group consisting of substituted acrylonitrile ultraviolet light absorbers and substituted benzotriazole ultraviolet light absorbers in a juvenile hormone containing composition, the activity of the juvenile hormone is prolonged even after several days in the field.

DETAILED DESCRIPTION OF THE INVENTION

As used throughout this application, the term "halogen" or "halo", when not expressly stated otherwise, includes all four halogens, i.e., fluorine, chlorine, bromine and iodine. As used herein, unless otherwise stated, the term "alkali metal" includes the metals of the first main group of the periodic chart, e.g., lithium, sodium and potassium. As also used herein, unless otherwise stated, the term "lower alkyl" comprehends both straight-chain and branched-chain saturated alkyl hydrocarbn groups containing from 1 to 6 carbon atoms, such as methyl, ethyl, propyl and isopropyl, with methyl and ethyl being preferred. The term "lower alkoxy", as used herein, unless otherwise stated, comprehends lower alkoxy groups containing from 1 to 6 carbon atoms such as methoxy, ethoxy and propoxy, with methoxy and ethoxy being preferred. The term "lower alkenyl", as used herein, unless otherwise stated, includes both straight-chain and branched-chain unsaturated alkenyl hydrocarbon groups having from 2 to 6 carbon atoms such as vinyl, allyl, butenyl and pentenyl, with allyl being preferred. The term "lower alkynyl", as used herein, unless otherwise stated, includes both straight-chain and branched-chain unsaturated hydrocarbon groups having from 2–6 carbon atoms such as ethynyl, propargyl and butynyl, with propargyl being preferred. The term "lower alkanoyloxy", as used herein, unless otherwise stated, comprehends lowr alkanoyloxy groups containing 1 to 6 carbon atoms, such as acetyloxy, formyloxy, butyryloxy, etc. The term "aryl", as used herein, unless otherwise stated, includes mono-nuclear aryl groups such as phenyl which can be unsubstituted or substituted in 1 or more positions with a hydroxy, lower alkylenedioxy, halogen, nitro, lower alkyl, lower alkoxy, lower alkynyl, lower alkynyloxy, lower alkenyl or lower alkenyloxy substituent, and polynuclear aryl groups such as naphthyl, anthryl, phenanthryl, azulyl, etc. which may be substituted with 1 or more of the aforementioned groups. The term "aryloxyloweralkyl" comprehends aryloxyloweralkyl groups wherein aryl is defined as above and the alkyl is lower alkyl. The preferred aryloxyloweralkyl group is phenyloxymethyl.

In accordance with this invention, a juvenile hormone can be stabilized against degradation caused by the effects of air and sunlight by adding thereto a substituted acrylonitrile ultraviolet light absorber (acrylonitrile u.v. absorber) or a substituted benzotriazole ultraviolet light absorber (benzotriazole u.v. absorber). A juvenile hormone can also be stabilized against degradation caused by the effects of air and sunlight by adding thereto a substituted phenolic anti-oxidant (phenolic anti-oxidant). By providing both an acrylonitrile or benzotriazole u.v. absorber and a phenolic anti-oxidant as additives to a juvenile hormone, the activity of a juvenile hormone can be maintained at a higher level for a greater period of time than is achieved by using an acrylonitrile or benzotriazole u.v. absorber or a phenolic anti-oxidant alone.

A juvenile hormone, stabilized in accordance with this invention, comprises a stabilized insecticide composition having greater and more activity after application in the field, that is useful for protecting foodstuffs, feed, textiles, plants and the like.

Any natural or synthetic juvenile hormone can be stabilized against degradation by the addition thereto of a phenolic anti-oxidant and/or an acrylonitrile or a benzotriazole u.v. absorber. The addition of the anti-oxidant and/or u.v. absorber is especially effective for stabilizing a juvenile hormone having an aliphatic chain with at least one carbon to carbon double bond and/or at least one oxygen or sulfur bridge. Among these juvenile hormones are included:

a compound of the formula:

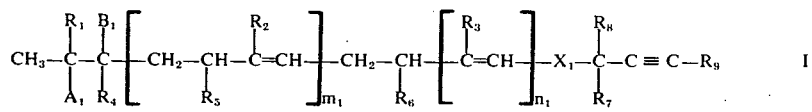  I wherein $R_1$ is methyl or ethyl; $R_2$ and $R_3$ are hydrogen, methyl or ethyl; $R_4$ is hydrogen or methyl; $R_5$ and $R_6$ are hydrogen or lower alkyl; $R_7$ and $R_8$ are hydrogen, methyl or ethyl; $R_9$ is hydrogen, lower alkyl, lower alkenyl, lower alkynyl or aryloxyloweralkyl;

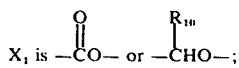

$R_{10}$ is hydrogen, methyl or ethyl; $A_1$ individually is hydroxyl; $B_1$ individually is chloro, bromo or iodo; and $A_1$ and $B_1$ taken together form a carbon to carbon bond, an oxygen bridge or sulfur bridge; and $m_1$ and $n_1$ are integers of from 0 to 1;

particularly, 10-11-epoxy-3.7, 11-trimethyl-1-(2-propynyloxy)-2,6-tridecadiene;

a compound of the formula:

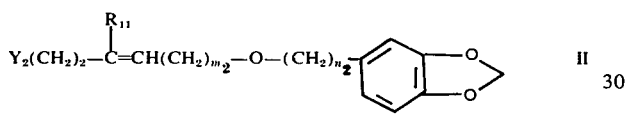  II wherein

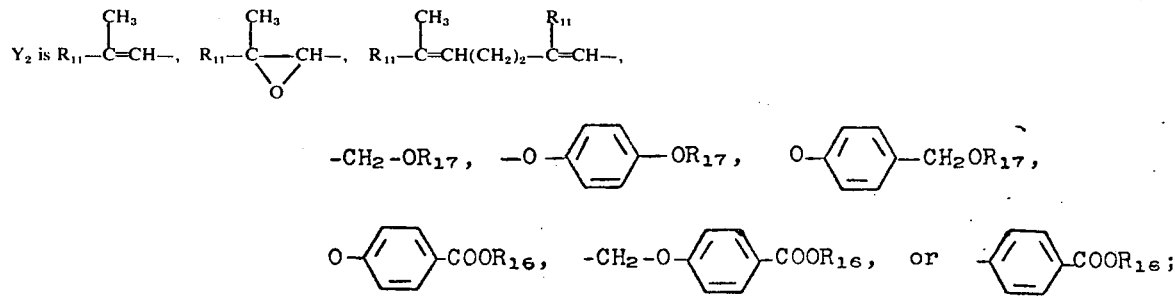

or

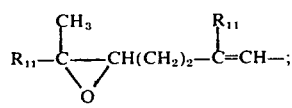

$m_2$ is an integer of from 1 to 2; $n_2$ is an integer of from 0 to 3; and $R_{11}$ is a straight-chain alkyl from 1 to 5 carbon atoms; with the proviso that when $m_2$ is 2, $n_2$ is 1 and $R_{11}$ is methyl,

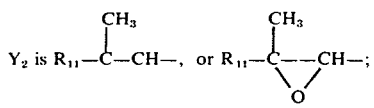

particularly, 6,7-epoxy-3,7-dimethyl-1-[3,4-(methylenedioxy)-phenoxy]-2-nonene;

a compound of the formula:

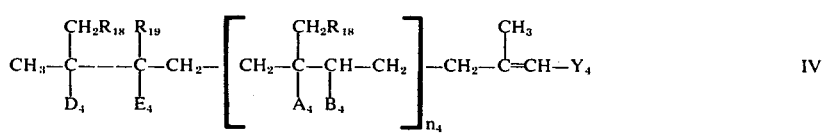  III wherein $R_{12}$ and $R_{13}$ are methyl or ethyl; $R_{14}$ and $R_{15}$ are hydrogen or methyl; $B_3$, $E_3$, $G_3$ and $J_3$ are individually hydrogen and $A_3$ and $D_3$ are individually hydrogen or halogen or $A_3$ and $B_3$ taken together from a carbon to carbon bond or an oxygen or sulfur bridge, $D_3$ and $E_3$ taken together form a carbon to carbon bond or a sulphur bridge, and $G_3$ and $J_3$ taken together form a carbon to carbon bond; $Y_3$ is $-COOR_{16}$, $R_{16}$ is hydrogen, lower alkyl, lower alkenyl, or lower alkynyl; $R_{17}$ is lower alkyl, lower alkenyl or lower alkynyl; and $m_3$, $n_3$ and $p_3$ are an integer of from 0 to 1;

particularly, methyl 10,11-epoxy-7-ethyl-3,11-dimethyl-2,6-tridecadienoate;

a compound of the formula:

IV wherein $A_4$ and $B_4$ are hydrogen or taken together form a carbon to carbon double bond or a sulfur bridge; $D_4$ and $E_4$ taken together form an oxygen or sulfur bridge; $R_{18}$ is hydrogen or lower alkyl; $R_{19}$ is lower alkyl; $X_4$ is a member selected from the group consisting of $-C \equiv N$, $-COOR_{20}$,

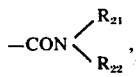

and —CH$_2$OR$_{23}$; R$_{20}$ is selected from the group consisting of hydrogen, phenyl, benzyl, lower alkyl, and substituted phenyl or benzyl; R$_{21}$ and R$_{22}$ are hydrogen or lower alkyl, or taken together with their attached nitrogen atom or a 5 or 6 membered heterocyclic ring containing at most one additional hetero atom selected from the group consisting of oxygen, nitrogen or sulfur; R$_{23}$ is hydrogen, lower alkyl, lower alkanoyl, benzoyl, lower alkyl substituted benzoyl, amino lower alkyl, lower alkyl substituted amino-lower alkyl, benzyl, phenyl, substituted benzyl, or substituted phenyl; and $n_4$ is an integer of from 0 to 1;

particularly, ethyl 10,11-epoxy-3,7,10,11-tetramethyl-2,6-dodecadienoate; and a compound of the formula:

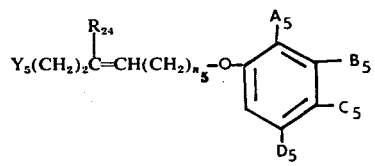

wherein Y$_5$ is selected from the group consisting of

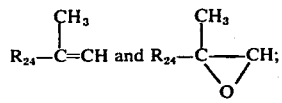

$n_5$ is an integer of from 1 to 2; R$_{24}$ is a straight chain alkyl radical from 1 to 5 carbon atoms; and A$_5$, B$_5$, C$_5$, and D$_5$ are members selected from the group consisting of hydrogen; oxygen; alkyl radicals containing from 1 to 5 carbon atoms; alkenyl radicals containing from 2 to 5 carbon atoms; halogen; —COCH$_3$; —COOCH$_3$; —OCH$_3$; —NO$_2$; —C≡N; —NH$_2$; —CH=O; and

particularly 6,7-epoxy-1-(p-ethylphenoxy)-3,7-dimethyl-2-octene. Among the preferred juvenile hormone type compounds of formulae I, II, III and IV are compounds of the formula:

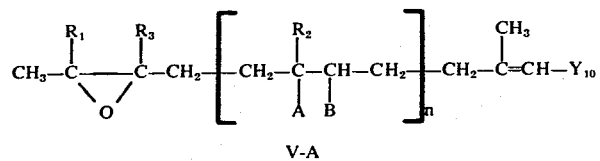

V-A wherein Y$_{10}$ is —COOR'$_{20}$, —CH$_2$—O—C≡CH

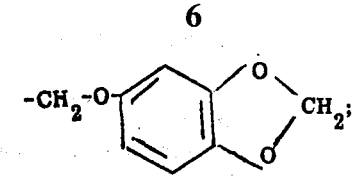

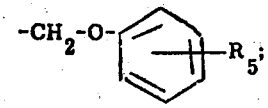

R$_1$, R$_2$, R$_3$ and R$_5$ are as above; R'$_{20}$ is hydrogen, or lower alkyl; A ad B are individualy hydrogen or taken together to form a carbon to carbon bond; and n is an integer of from 0 to 1.

In accordance with this invention, any conventional substituted phenolic anti-oxidant can be utilized. Among the preferred phenolic anti-oxidants are the phenolics substituted with hydroxy, lower alkyl or lower alkoxy, particularly in the ortho and/or para positions, such as nordihydroguaiaretic acid (NDGA), butylated hydroxyanisole (BHA), and butylated hydroxytoluene (BHT). Quite particularly preferred phenolic anti-oxidants are NDGA and BHA, especially a mixture of NDGA and BHA.

In accordance with this invention, any conventional substituted benzotriazole ultraviolet light absorber can be utilized. Among the preferred benzotriazole u.v. absorbers are the u.v. absorbers shown in U.S. Pat. Nos. 3,076,782; 3,159,646; 3,189,615; 3,214,436 and 3,218,332, particularly, the benzotriazole ultraviolet light absorbers, shown in U.S. Pat. No. 3,189,615, having the formula:

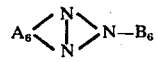 VI wherein A$_6$ is an o-phenylene group bound by two neighboring carbon atoms to two nitrogen atoms of the triazole ring, said o-phenylene group being selected from the group consisting of unsubstituted o-phenylene, o-phenylene carboxylic acid(lower)alkyl ester, ethyl sulphonyl-o-phenylene, chloro-o-phenylene, lower alkoxy-o-phenylene, and lower alkyl-o-phenylene; and B$_6$ is 2-hydroxyphenyl substituted by a member selected from the group consisting of lower alkyl, lower alkoxy, lower carbalkoxy, cyclohexyl, phenyl and chlorine.

Among the particularly preferred u.v. absorbers of formula VI, quite particularly preferred are the compounds wherein A$_6$ is unsubstituted o-phenylene or chloro-o-phenylene and B$_6$ is substituted by lower alkyl, such as 2-(3',5'-ditertbutyl-2'-hydroxy-5'-methylphenyl)-5-chlorobenzotriazole.

In accordance with this invention, the preferred, u.v. absorbers are the substituted acylonitrile ultraviolet light absorbers. Any conventional acrylonitrile u.v. absorber can be utilized [see Rossman et al., "Acrylonitriles, A New Group of Ultraviolet Absorbing Compounds", *The Journal of Investigative Dermatology*, vol. 39, No. 5, pp. 449–453 (1962)]. Among the preferred acrylonitrile u.v. absorbers are the acrylonitrile u.v. absorbers shown in U.S. Pat. No. 3,074,971; 3,275,520; 3,462,475; 3,576,005; 3,523,953; and 3,576,003. Particularly preferred are the acrylonitrile u.v. absorbers, shown in U.S. Pat. No. 3,275,520, having the formula:

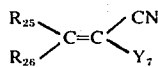   VII wherein $R_{25}$ is selected from the group consisting of hydrogen, alkyl, aryl, alkehyl and hetero; $Y_7$ is selected from the group consisting of —CN and

$X_7$ is selected from the group consisting of —$OR_{27}$ and

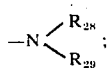

$R_{27}$, $R_{28}$ and $R_{29}$ are selected from the group consisting of hydrogen, alkyl, aryl, alkenyl, and hetero; and $R_{26}$ is selected from the group consisting of aromatic carbocyclic nuclei and heterocyclic nuclei having at least one pair of conjugated double bonds.

Among the particularly preferred acrylonitrile u.v. absorbers of formula VII, quite particularly preferred are the compounds wherein $R_{25}$ and $R_{26}$ are aryl and $Y_7$ is

particularly ethyl-2-cyano-3,3-diphenyl acrylate and 2-ethyl-hexyl-2-cyano-3,3-diphenyl acrylate.

In accordance with this invention, stabilized insecticide compositions can be prepared which contain: one or more juvenile hormone compounds as an active ingredient; a phenolic anti-oxidant; and/or an acrylonitrile or benzotriazole u.v. absorber. The proportions of the components of the synergistic insecticides composition, in accordance with this invention, may vary within wide limits according to the purpose of use, the mode of application, the pests to be controlled, the environment to be covered and other factors. Any effective ratio of the juvenile hormone, anti-oxidant and ultraviolet light absorber can be utilized. However, it is preferred to use approximately 10–75 percent by weight of juvenile hormone and 1–20 percent by weight of u.v. absorber, with about 25–50 percent by weight of juvenile hormone and 5–10 percent by weight of u.v. absorber being particularly preferred. In accordance with a more preferred embodiment of this invention, it has been found that the stability of juvenile hormones can be even further enhanced by utilizing an insecticide composition comprising approximately 10–75 percent by weight of juvenile hormone, 1–25 percent by weight of anti-oxidant and 1– 20 percent by weight of u.v. absorber, with about 25–50 percent by weight of juvenile hormone, 2–5 percent by weight of anti-oxidant and 5–10 percent by weignt of u.v. absorber being particularly preferred.

Pest control agents, containing the stabilized insecticide composition in accordance with this invention, can be prepared in the form of granulates, concentrates or ready-to-use pest control agents. The concentration of the insecticide composition depends upon the form of pest control agent and the mode of use. The pest control agents in accordance with this invention can contain solid or liquid inert carrier materials to form solutions, sprays, aerosols or dusting powders. For these pest-control agents, it may be advantageous for the insecticide composition to be in the form of an emulsion, a suspension, or a solution with the carrier material and to further include emulsifying and/or wetting agents. In preparing an emulsion, the stabilized insecticide composition is preferably dissolved in 5 to 50 percent by weight of an emulsifier, with 10 to 20 percent by weight of the emulsifier being particularly preferred. Solutions of the stabilized insecticide compositions, suitable as sprays for a material to be protected, can be prepared by dissolving or dispersing the stabilized insecticide compositions in a liquid solvent such as: mineral oil fractions, cold tar oils, oils of vegetable or animal origins, hydrocarbons, such as napthanes, ketones, such as methyl ethyl ketone and acetone, or chlorinated hydrocarbons such as tetrachloroethylene, tetrachlorobenzene, and the like. Suitable dusting powders can be obtained by combining the stabilized insecticide composition with solid carrier materials, preferably porous carrier materials such as: chalk, talc, bentonite, kaolin, diatomacious salt, silicaeous earth, fuller earth, lime, gypsum, powders and meals from organic waste products, etc.

In general, the pest-control agents utilizing the stabilized insecticide compositions of the present invention can be prepared according to a process such as is described, for example, in *Farm Chemicals*, vol. 128, pages 52 ff. The pest-control agents in accordance with this invention can additionally utilize yet other additives such as masking agents.

The pest-control agents in accordance with this invention can exist in the form of concentrates which are suitable for storge and transport. Such concentrates can, for example, contain 10–18% by weight of the stabilized insecticide composition of this invention, as the active substance, and 90–20% by weight of an inert carrier material. In preparing these concentrates, any conventional, liquid or solid inert carrier material can be utilized. Among the inert carrier materials which can be utilized are the liquid solvents and solid materials mentioned above.

These concentrates can be further divided with similar or different carrier materials to concentrations which are suitable for practical use as ready-to-use pest-control agents. In the ready-to-use agents, the concentration of the stabilized insecticide composition of this invention is preferably 0.01–20 weight percent and the concentration of the carrier material is preferably 99.99–80 weight percent, with 0.1–10 weight percent of the stabilized insecticide composition and 99.9–90 weight percent of the carrier material being especially preferred. The concentration of the stabilized insecticide composition can also be smaller or larger than the preferred concentration. In preparing these ready-to-use pest-control agents, any conventional liquid or solid inert carrier material may be utilized. Among the inert carrier materials which may be utilized are the liquid and solid materials mentioned above.

The conventional, inert carrier materials utilized in combination with the insecticide composition of this invention are substances which are used to dissolve, disperse or diffuse the components of the stabilized insecticide compositions of this invention without impairing their individual effectiveness or their synergism. In addition, these carrier materials do not permanently damage the environment to which they are applied (e.g., crops, soil, equipment, etc.). Preferably, the carrier materials ae also water immiscible, aromatic hydrocarbons and ketones being the preferred liquid solvents set forth above.

The ready-to-use pest-control agents of this invention may be advantageously applied to certain plants, foodstuffs, textiles and the lke. An effective amount of the pest-control agent can be applied to an insect-infested area using any conventionally acceptable method such as spraying, dusting, etc. The choice of the concentration of the stabilized insecticide composition in the pest-control agent and the rate of application to the insect-infested area will, of course, depend on several factors, for example, the type and maturity of insects present, the type of pest-control agent and the mode of application. Generally, in combatting insects, the stabilized insecticide composition of this invention can be advantageously applied to the material to be protected in concentrations of about $10^{-3}$ to $10^{-6}$ g/cm$^2$ of the material to be protected, preferably $10^{-4}$ to $10^{-5}$ g/cm$^2$.

The juvenile hormones of formula I can be prepared through the reaction of a compound of the formula:

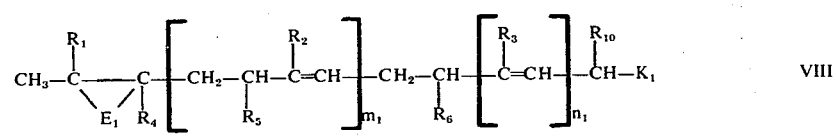

with a compound of the formula:

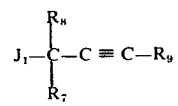

wherein $R_1$, $R_2$, $R_3$, $R_4$, $R_5$, $R_6$, $R_7$, $R_8$, $R_9$, $R_{10}$, $m_1$ and $n_1$ are as above; $E_1$ is a carbon to carbon bond, a sulfur bridge or an oxygen bridge; and one of $J_1$ and $K_1$ is chloro, bromo or iodo and the other is hydroxy;

to produce a compound of the formula:

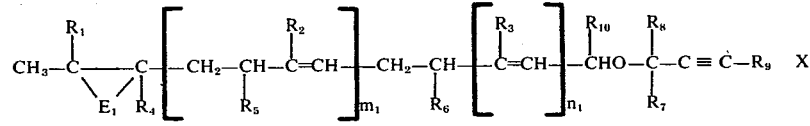

wherein $R_1$, $R_2$, $R_3$, $R_4$, $R_5$, $R_6$, $R_7$, $R_8$, $R_9$, $R_{10}$, $E_1$, $m_1$ and $n_1$ are as above;

or through the reaction of a compound of the formula

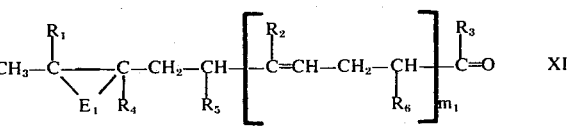

wherein $R_1$, $R_2$, $R_3$, $R_4$, $R_5$, $R_6$, $E_1$ and $m_1$ are as above; with a compound of the formula

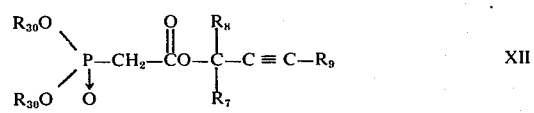

wherein $R_7$, R8 and $R_9$ are as above; and $R_{30}$ is lower alkyl, phenyl lower alkyl, halophenyl lower alkyl or lower alkoxyphenyl lower alkyl;

to produce a compound of the formula:

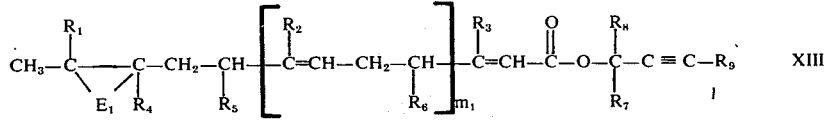

wherein $R_1$, $R_2$, $R_3$, $R_4$, $R_5$, $R_6$, $R_7$, $R_8$, $R_9$, $E_1$ and $m_1$ are as above.

The reaction of the compound of formula VIII with a compound of the formula IX can be carried out in the presence of an inert organic solvent. In carrying out this reaction, any conventional inert organic solvent can be utilized, such as benzene, toluene, dioxane or 1,2-dimethoxyethane. Generally, it is preferred to cary out this reaction utilizing an inert organic solvent such as tetrahydrofuran and an aprotic solvent. Any conventional aprotic solvent, preferably hexamethylphosphoric acid triamide, can be utilized, In carrying out this reaction, temperature and pressure are not critical, and a temperature of from 0°C. to the reflux temperature of the reaction medium can be utilized. Generally, a reaction temperature of 70°C. is preferred since the reaction components dissolved in tetrahydrofuran will reflux under these conditions. In carrying out this reaction, the hydroxyl group of either $J_1$ or $K_1$ is converted to its alkali metal salt. The conversion of the alcohol to the corresponding alkali metal salt can be carried out by conventional procedures well known in the art. In accordance with a preferred embodiment, the compound of formula VIII or IX, where either $J_1$ or $K_1$ is a hydroxyl group, is reacted with a suitable base or alkali metal such as sodium hydride, potassium t-butylate, utilizing tetrahydrofuran as the solvent. This alkali metal salt is then reacted with the halide of either compound VIII or compound IX to prepare the compound of the formula X.

The reaction of the compound of formula XI with a phosphine oxide of the formula XII can be carried out in the presence of a base in an inert organic solvent medium. Any conventional base such as an alkali metal hydride which includes sodium hydride, etc.; or alkali metal alcoholate such as sodium methylate can be utilized in carrying out this reaction. Furthermore, in carrying out this reaction, any conventional inert organic solvent can be utilized. If sodium hydride is utilized as the base, solvents such as benzene, toluene, dimethylformamide, tetrahydrofuran, dioxane or 1,2-methoxyethane are preferred. If this reaction is carried out in the presence of an alkali metal alcoholate such as sodium methylate, alcohol solvents such as methanol are preferred. In carrying out this reaction, temperature and pressure are not critical and this reaction can be carried out at room temperature and atmospheric pressure. Generally, it is preferred to carry out this reaction at a temperature of from about 0°C. In a particularly preferred embodiment, the compound of formula XI is reacted with a compound of formula XII in the presence of 2 moles of sodium hydride in absolute tetrahydrofuran. The excess sodium hydride can be destroyed by the addition of an absolute alkanol before further processing.

The compound of formula I wherein $A_1$ and $B_1$ taken together form a carbon to carbon bond can be epoxidized to the compound of formula I, wherein $A_1$ and $B_1$ taken together form an oxygen bridge, by any conventional epoxidization procedure. Generally, this reaction is carried out by dissolving the unsaturated compound of formula I in an inert organic solvent and treating this solution with a peracid. In carrying out this reaction, any conventional inert organic solvent, particularly the halogenated hydrocarbon solvents such as chloroform or carbon tetrachloride, can be utilized. Generally, the preferred solvent in this reaction is methylene chloride. Any conventional peracid can be utilized in carrying out the epoxidization reaction. Among the conventional peracids which can be utilized are included: performic acid, peracetic acid, perbenzoic acid, and perphthalic acid. In carrying out the epoxidization reaction, m-chloroperbenzoic acid is the preferred peracid. In carrying out this reaction, temperature and pressure are not critical, and this reaction can be carried out at a temperature of from 0°C. to 40°C.

The compound of formula I, wherein $A_1$ and $B_1$ taken together form an oxygen bridge, can be converted to the corresponding epithio compound of formula I, wherein $A_1$ and $B_1$ taken together form a sulfur bridge, by episulfidization in two steps. In the first step, the epoxide of formula I is reacted with an episulfidizing agent in the presence of a mineral acid at a temperature of from 0°C. to 30°C. to form the isothiouronium salt. In the second step, the isothiouronium salt is cleaved to form the epithio compound by means of treatment with a base.

In the first step of this reaction, the epoxide of formula I can be reacted with an episulfidizing agent in the presence of a mineral acid at a temperature of from 0°C. to 30°C. Generally, it is preferred to utilize temperatures of from 0°C. to 5°C. in carrying out this reaction. Any conventional mineral acid can be utilized such as sulfuric acid, hydrochloric acid, etc. The preferred acid is an aqueous sulfuric acid such as 2N aqueous sulfuric acid. Any conventional episulfidizing agent such as the episulfidizing agents mentioned hereinbefore can be utilized. Thiourea is the preferred episulfidizing agent. In carrying out this reaction, an inert organic solvent can be utilized. Any conventional inert organic solvent can be utilized. Among the inert organic solvents, dioxane is preferred.

The isothiouronium salt thus formed can be cleaved to form the epithio compound of formula I by treating the isothiouronium salt with a base. Any of the conventional bases such as those hereinbefore mentioned can be utilized. Among the conventional bases which can be utilized are the alkali metal carbonates, with sodium carbonate and potassium carbonate being preferred. Generally, these carbonates are added in the form of an aqueous solution. Generally, this cleavage of the isothiouronium salt is carried out in the solvent system which was utilized for its formation. Therefore, organic polar solvents such as methanol and ethanol are preferred. In carrying out this cleavage reaction, temperature and pressure are not critical and this reaction can be carried out at room temperature and atmospheric pressure. However, higher or lower temperatures can be utilized. Any temperature from about 0°C. to the reflux temperature of the reaction mixture can be utilized. However, temperatures of from 0°C. to 5°C. are generally preferred.

The compound of formula I, wherein $A_1$ individually is hydroxy and $B_1$ individually is chloro, bromo or iodo, can be prepared by hydroxyhalogenating the compound of the formula I, wherein $A_1$ and $B_1$ taken together form a carbon to carbon bond. This hydroxyhalogenation can be carried out by conventional procedures. In accordance with a preferred embodiment of this invention, the unsaturated compound of formula I is suspended in water and treated with an equal amount of an inert organic solvent to form a homogeneous concentrated solution. In accordance with this invention, any conventional inert organic solvent can be utilized. Among the conventional inert organic solvents which can be utilized are included: dioxane, 1,2-dimethoxyethane and tetrahydrofuran with tetrahydrofuran being preferred. This solution can be treated with a conventional hydroxyhalogenating agent to hydroxyhalogenate the unsaturated compound of formula I. If it is desired to produce a compound of the formula I wherein $B_1$ is bromine, N-bromosuccinimide can be added to the solution at a temperature of from about 0°C. to 40°C. If it is desired to produce a compound of the formula I where $B_1$ is chlorine or iodine, N-chlorosuccinimide or N-iodosuccinimide can be utilized as the hydroxyhalogenating agent with temperatures of from 0°C. to 5°C.

The terpenoid side chains of the juvenile hormone of formula II can be prepared by the Marc Julia synthesis [Bull. Soc. Chem. France 1072, (1960)] as outlined below.

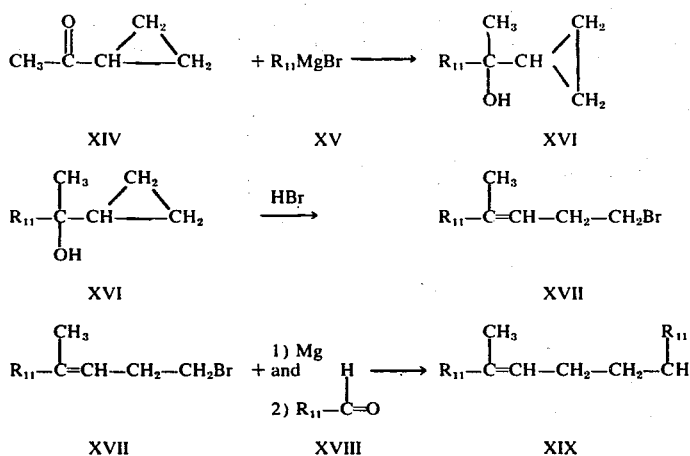

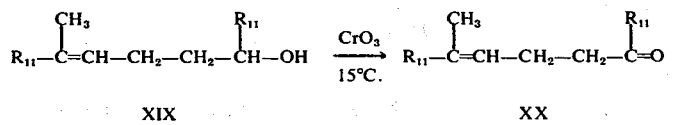

Oxidation can be accomplished with chromic acid solution in acetone [J. Chem. Soc. 2548 (1953)] as outlined below.

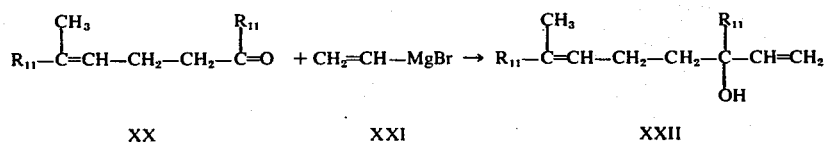

The corresponding vinyl analogs can be prepared by the Grignard reaction with vinyl magnesium bromide (or chloride) in tetrahydrofuran as outlined below.

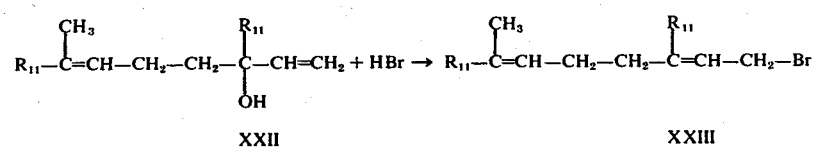

The vinyl analogs can be converted to the bromides by treatment with hydrogen bromide in acetic acid as outlined below. Thus, an aliquot of the vinyl analog can be stirred in an ice bath at 5°C. in an organic solvent such as hexane, benzene, diethyl ether or dichloromethane during the dropwise addition of two molar equivalents of hydrogen bromide as a 30% solution in acetic acid. After the addition of HBr the reaction mixture can be poured into an excess of ice cold, 5% by weight aqueous sodium carbonate, extracted with diethyl ether and washed to neutrality with water. After drying the ethereal extracts over sodium sulfate and removal of the solvent in vacuo, the bromide can be obtained in nearly quantitative yield.

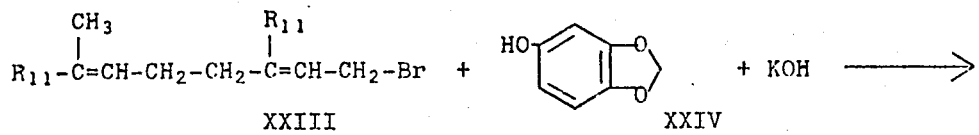

The bromides can be refluxed for 3–5 hours with a slight molar excess of sesamol and potassium hydroxide in a 1:1 mixture of 95% ethanol and dimethoxyethane to yield the sesamolyl ethers as outlined below.

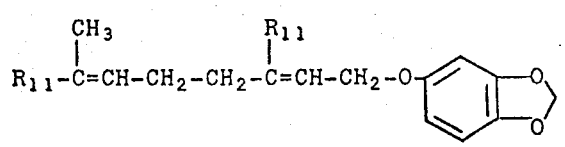

The bromides can be refluxed with a slight molar excess of potassium tert-butoxide and piperonyl alcohol in dimethoxyethane for 3–5 hours to yield the piperonyl ethers.

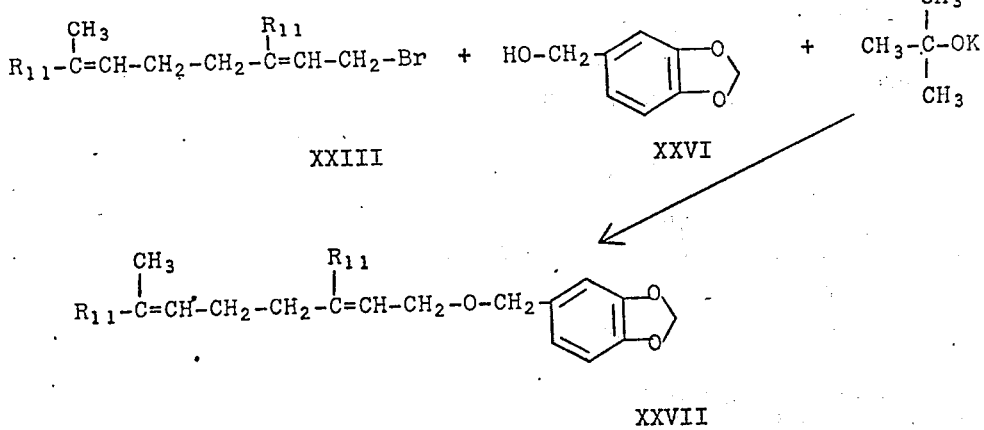

XXIII    XXVI

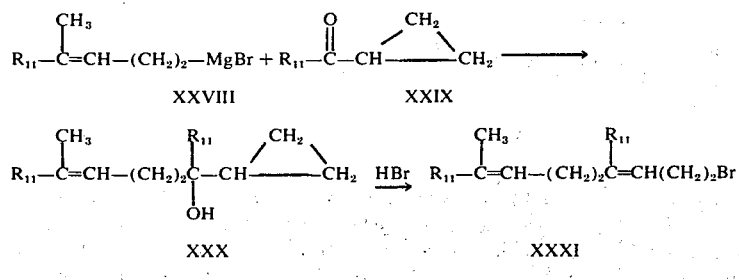

XXVII

In all of the above reactions, from the preparation of the terpenoid side chains to the preparation of the sesamolyl and piperonyl ethers, $R_{11}$ is as above.

Another series of compounds in which the carbon chain was one carbon longer can be prepared in a similar manner except that the bromides were prepared by a continuation of the Marc Julia synthesis as outlined below.

in which $R_{11}$ is as above.

The sesamolyl and piperonyl ethers can be expoxidized to a compound of formula II wherein $Y_2$ is

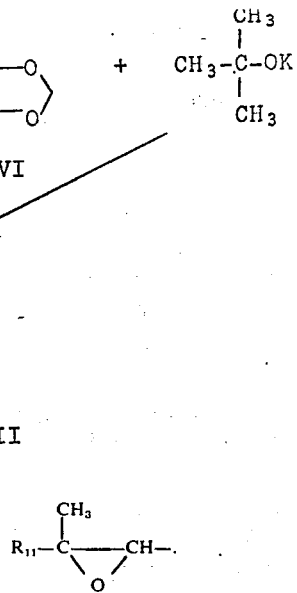

Epoxidization can be carried out by the procedure utilized for epoxidizing a compound of the formula I wherein $A_1$ and $B_1$ taken together form a carbon to carbon bond.

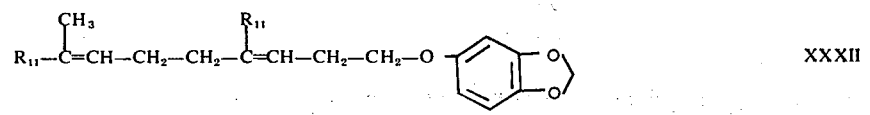

XXVIII    XXIX

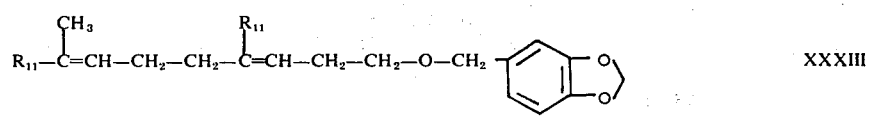

XXX    XXXI

The sesamolyl and piperonyl ethers prepared from the bromides had the following several formulas:

The sesquiterpenoid side chains of the general formula

XXXII and

XXXIII

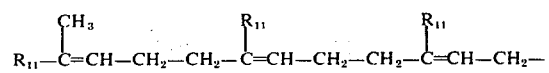

XXXIV in which $R_{11}$ is as above, can be prepared from the bromides via the acetoacetic ester synthesis, as outlined below,

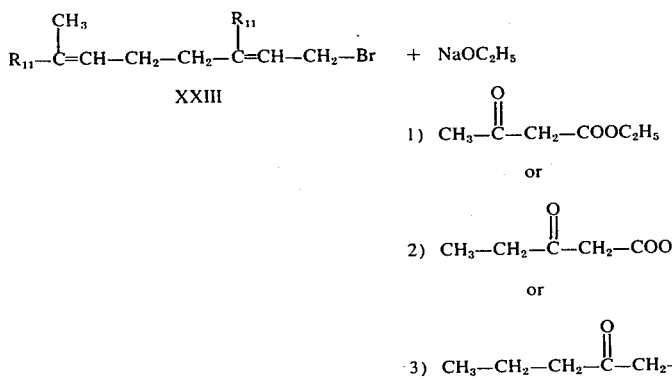
XXIII

1) $CH_3-\overset{O}{\overset{\|}{C}}-CH_2-COOC_2H_5$  XXXV A or

2) $CH_3-CH_2-\overset{O}{\overset{\|}{C}}-CH_2-COOC_2H_5$  XXXV B or

3) $CH_3-CH_2-CH_2-\overset{O}{\overset{\|}{C}}-CH_2-COOC_2H_5$  XXXV C to yield the corresponding keto esters

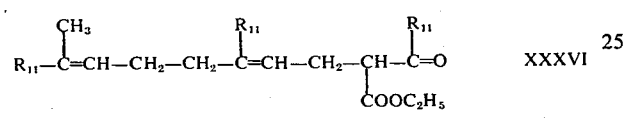 XXXVI which after reflux with 5% by weight aqueous sodium hydroxide (1–2 hours) yields the decarboxylated ketone

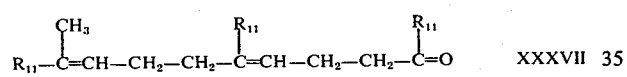 XXXVII

Reaction of these ketones with vinyl magnesium bromide (or chloride) in tetrahydrofuran followed by synthesis of the bromide with hydrogen bromide gives bromides of the following general formula:

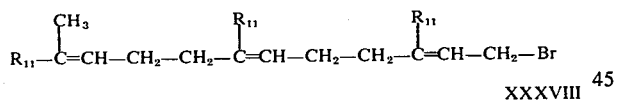 XXXVIII

The sesamolyl and piperonyl ethers and their epoxides can then be prepared as outlined previously for the terpenoid compounds.

The juvenile hormones of formula III can be obtained by reacting a compound of the formula:

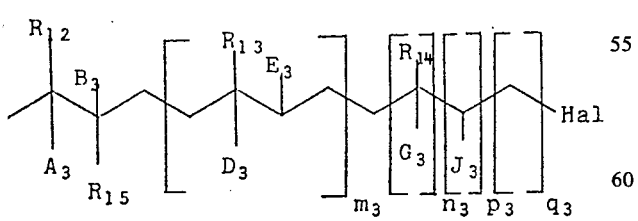
XXXIX wherein $R_{12}, R_{13}, R_{14}, R_{15}, A_3, B_3, D_3, E_3, G_3, J_3, m_3, n_3$ and $p_3$ are as above; $q_3$ is an integer of from 0 to 1 and Hal is a halogen;

with a compound of the formula $M-Y_3'$  XL wherein M is an alkali metal; $Y_3'$ is and

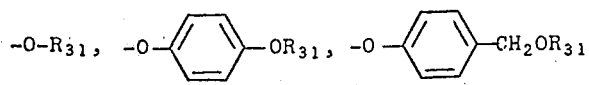

or 

wherein $R_{31}$ is hydrogen, lower alkyl, lower alkenyl, or lower alkynyl;

to form a compound of the formula:

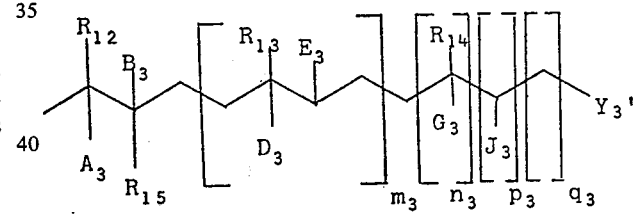
XLI wherein $R_{12}, R_{13}, R_{14}, R_{15}, A_3, B_3, D_3, E_3, G_3, J_3, m_3, n_3, p_3, q_3$ and $Y_3'$ are as above.

The juvenile hormones of formula III can also be obtained by reacting a compound of the formula:

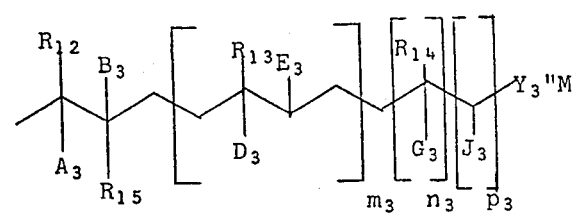
XLII wherein $R_{12}, R_{13}, R_{14}, R_{15}, A_3, B_3, D_3, E_3, G_3, J_3, m_3, n_3$ and $p_3$ are as above; M is an alkali metal as above; and $Y_3''M$ is $-COO-M$,.

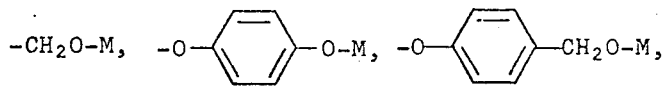

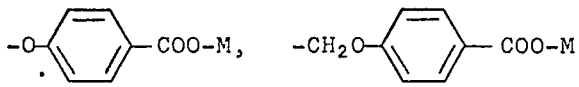

or 

with a compound of the formula:

R₃₂—Hal　　　　　　　　　　　　　　XLIII wherein Hal is as above and $R_{32}$ is lower alkyl, lower alkenyl or lower alkynyl;
to form a compound of the formula:

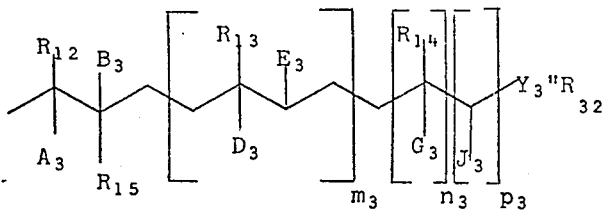

wherein $R_{12}$, $R_{13}$, $R_{14}$, $R_{15}$, $A_3$, $B_3$, $D_3$, $E_3$, $G_3$, $J_3$, $m_3$, $n_3$, $p_3$, $Y_3''$ and $R_{32}$ are as above.

The halide compound of formula XXXIX can be reacted with an alkali metal salt of formula XL in an inert solvent, preferably in the presence of an aprotonic solvent. In carrying out this reaction, any conventional inert organic solvent can be utilized, with benzene, toluene, dioxane, 1,2-dimethoxymethane and tetrahydrofuran being preferred and tetrahydrofuran being especially preferred. In this reaction, any conventional aprotonic solvent can be utilized, with hexamethyl phosphoric acid triamide being preferred. In this reaction, temperature and pressure are not critical, and the reaction can be suitably carried out in a temperature range of 0°C. to the boiling point of the reaction mixture. In a preferred embodiment of this reaction, the reaction is carried out at ca 70°C., the reflux temperature of the especially preferred solvent.

The alkali metal salt of formula XLII can be reacted with the halide of formula XLIII in an inert solvent, preferably in the presence of an aprotonic solvent. In carrying out this reaction, any conventional inert organic solvent can be utilized, with benzene, toluene, dioxane, 1,2-dimethoxymethane and tetrahydrofuran being preferred and tetrahydrofuran being especially preferred. In this reaction, any conventional aprotonic solvent may be utilized, with hexamethyl phosphoric acid triamide being preferred. In this reaction, temperature and pressure are not critical, and the reaction can be suitably carried out in a temperature. range of 0°C. to the boiling point of the reaction mixture. In a preferred embodiment of this reaction, as in the above reaction, the preferred temperature is ca 70°C.

XLIV

The reaction mixtures from the reactions of either a compound of formula XXXIX with a compound of formula XL or a compound of the formula XLII with a compound of formula XLIII can be worked up in a conventional manner to obtain the juvenile hormones of formula III. A preferred method of working up includes: pouring the reaction mixture onto ice; extracting the compound of formula III with a conventional inert organic solvent, preferably diethyl ether; washing the solvent extract with water; drying the solvent and evaporating the solvent. The residual compound of formula III can be further purified by adsorption, preferably on Kieselgel or aluminum oxide.

The epoxidation of a compound of formula III wherein $A_3$ and $B_3$ taken together form a carbon to carbon bond can be expediently carried out in the same manner as the epoxidation of a compound of formula I, as set forth above. The epoxide compound of formula III can be converted to the corresponding epithio compound of formula III in the same manner as the conversion of the epoxide compound of formula I to an epithio compound of formula I, as set forth above.

The compounds of formula IV above can be prepared by reacting a compound of the formula:

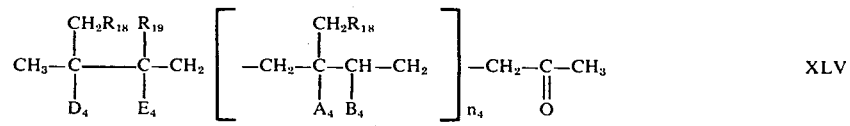　　　　　　XLV wherein $R_{18}$, $R_{19}$, $A_4$, $B_4$, $D_4$, $E_4$ and $n_4$ are as above; with a phosphine oxide of the formula:

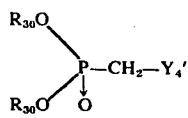 XLVI wherein $Y_4'$ is selected from the group consisting of $-C\equiv N$; $-COOR_{20}'$; and

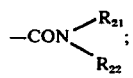

$R_{20}'$ is lower alkyl, phenyl, benzyl or substituted phenyl and benzyl; and $R_{21}$, $R_{22}$ and $R_{30}$ are as above.

The reaction of a compound of formula XLV with a compound of formula XLVI can be carried out in the presence of an alkali metal base in an inert organic solvent. Any conventional alkali metal base can be utilized. Among the conventional alkali metal bases are included alkali metal hydrides such as sodium hydride or potassium hydride; alkali metal lower alkoxides such as sodium methoxide, sodium ethoxide, etc.; and the alkali metal amide bases such as sodamide, potassium amide, sodium methyl amide, potassium methyl amide, as well as other alkali metal lower alkyl amides. In carrying out this reaction, any inert organic solvent can be utilized such as benzene, toluene, N,N-dimethylformamide, tetrahydrofuran, dioxane and 1,2-dimethoxyethane. In carrying out this reaction, a temperature of from 0°C. to 30°C. should be utilized.

Where $R_{20}$ is lower alkyl in the compound of formula IV, the compound can be converted to the free acid by any conventional technique or ester hydrolysis or saponification such as treatment with an alkali, e.g., sodium hydroxide.

The alcohol and esters of formula IV wherein $Y_4$ is $-CH_2OR'_{23}$, wherein $R'_{23}$ is lower alkyl, lower alkanoyl, benzoyl, lower alkyl substituted benzoyl, amino lower alkyl, lower alkyl substituted amino, benzyl, phenyl, substituted benzyl, or substituted phenyl, can be prepared from an alcohol of the formula:

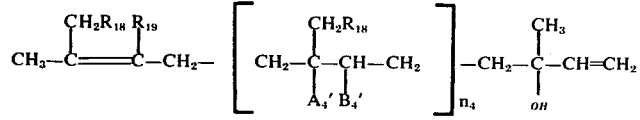 XLVII wherein $R_{18}$, $R_{19}$ and $n_4$ are as above; and $A'_4$ and $B'_4$ are hydrogen or taken together form a carbon to carbon double bond;

by the following reaction scheme:

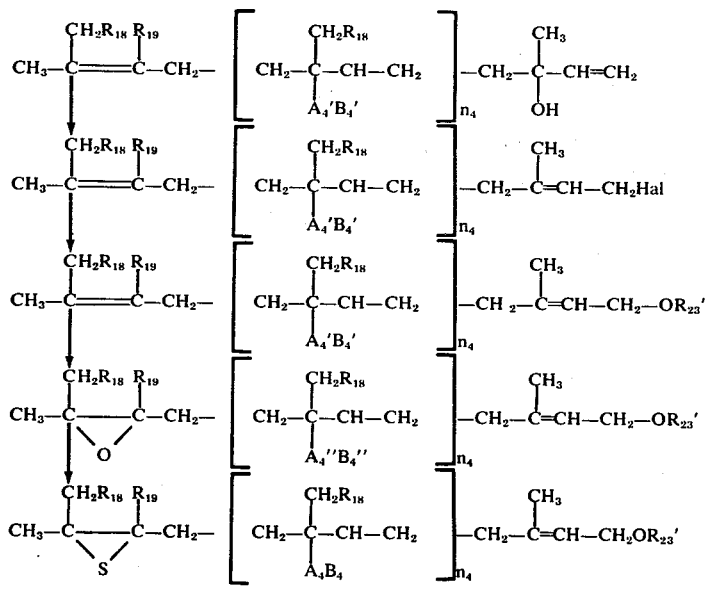

wherein $A'_4$ and $B'_4$, $A_4$ and $B_4$, $R_{18}$, $R_{19}$, $R'_{23}$ and $n_4$ are as above; Hal is a halogen; and $A''_4$ and $B''_4$ are individually hydrogen or taken together from a carbon to carbon double bond or an oxygen bridge.

The compounds of formula XLVII above can be converted to the compound of formula XLVIII above by subjecting the compound of formula XLVII to halogenation in the presence of a base. Any conventional method of halogenation can be utilized in carrying out this reaction. Generally, the halogenation can be carried out by treating the compound of formula XLVII with a halogenating agent such as a thionyl halide or a phosphorous trihalide in the presence of a base. Among the preferred halogenating agents are included phosphorous tribromide, phosphorous pentachloride, thionyl chloride, etc. Any conventional base such as the bases mentioned hereinbefore can be utilized in carrying out this reaction. Among the preferred bases are included the tertiary amines such as pyridine. In carrying out this reaction, an inert organic solvent medium is generally utilized. Any conventional inert organic solvent such as hexane or diethyl ether can be utilized. Furthermore, this reaction is generally carried out at a temperature of from about −15°C. to 30°C.

The compound of formula XLVIII can be converted to the compound of formula IL by reacting the compound of formula XLVIII with a compound of the formula:

$$MO—R'_{23} \qquad \text{LII}$$

wherein M is an alkali metal as above and $R'_{23}$ is as above.

Any of the conditions conventional in reacting alkali metal alcoholates or alkali metal alkanoates with primary halides can be utlized in carrying out this reaction.

The compound of formula IL can be converted into the compound of formula L by epoxidation. Epoxidation can be carried out in the manner utilized above for epoxidizing a compound of formula I. The compound of formula L wherein $A''_4$ and $B''_4$ taken together form a carbon to carbon double bond can be converted to a compound of formula LI by episulfidization Episulfidization be carried out in the manner described above for episulfidizing a compound of formula I.

The compounds of formula IV wherein $R_{23}$ is lower alkyl, benzoyl or lower alkyl substituted benzoyl can be converted by saponification to the free alcohol, i.e., where $R_{23}$ is hydrogen. Any conventional method of ester saponification can be utilized in converting such compounds to the free alcohol.

The terpenoid portion of the juvenile hormones of formula V can be prepared by the Marc Julia synthesis [Bull. Soc. Chem. France 1072, (1960)] as outlined below.

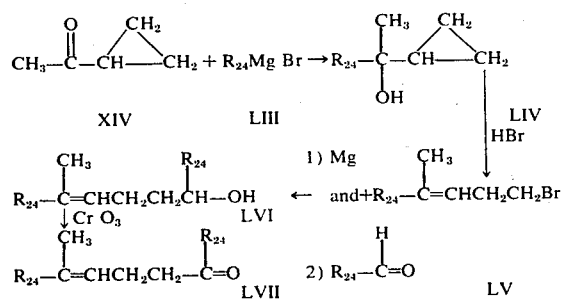

Grignard reaction of the resulting ketone with vinyl magnesium chloride (or bromide) in tetrahydrofuran gives the vinyl alcohol, which can be converted to the allylic bromide, as outlined below,

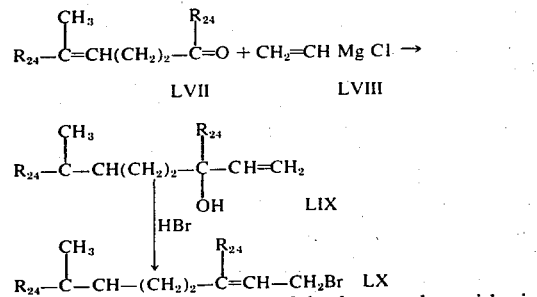

by stirring with an excess of hydrogen bromide in aqueous or acetic acid media. [W. S. Bowers, Science 164, 323 (1969)]. In the reactions above, $R_{24}$ is as above.

The ethers of formula V can be prepared by refluxing the resulting bromides with a slight molar excess of the desired alcohol and excess powdered potassium hydroxide in dimethoxyethane or dimethylformamide for 2–10 hours, as in the preparation of the ethers of formula II, above. The reaction mixture can be extracted with diethyl ether or hexane and washed with water. The diethyl ether or hexane portion can be dried over anhydrous sodium sulfate. Removal of the solvent in vacuo yields the crude ethers. All compounds can be purified by column chromatography over Florisil. The compounds can be put on the column in hexane and eluted stepwise with increasing concentrations of diethyl ether in hexane.

The ethers can be epoxidized by stirring them in an organic solvent such as benzene, chloroform or methylene chloride during the addition of a slight molar excess of an epoxidizing agent such as m-chloroperbenzoic acid in the manner set forth above with regard to the epoxidation of the compound of formula I.

The examples which follow illustrate the invention. All temperatures are stated in degrees centigrade. Florisil is a highly selective adsorbent or magnesia-silica gel. Percents are by weight. Nujol is mineral oil, and the percent of hydride in the mineral oil suspension is given as percent by weight.

EXAMPLE 1

1.5 g. sodium hydride (50% Nujol suspension) are washed twice with 10 ml. portions of hexane and covered with a layer of 10 ml. absolute tetrahydrofuran. 8 g. 10,11-epoxy-3,7,11-trimethyl-2,6-tridecadien-1-ol are added dropwise to this mixture in such a manner that the temperature does not exceed 30°. The mixture is stirred for 1 hour at room temperature. Then 4.2 g. propargyl bromide and, with ice cooling, 12 ml. hexamethylphosphoric triamide are added dropwise in this order; stirring is continued for 2.5 hours at 50°. The mixture is poured on saturated aqueous sodium chloride solution and processed as described in Example 4. Chromatography on silica gel with hexane and ether (8:2 parts by volume) and distillation under high vacuum yields 10,11-epoxy-3,7,11-trimethyl-1-(2-propynyloxy)-2,6-tridecadiene. Boiling point 113°–116°/0.001 mmHg; $n_D^{20}$: 1.4846.

EXAMPLE 2

A solution of 246 g. of sesamol in 1.8 liters of dimethylformamide contained in a 3 l. four-necked flask (with stirrer, dropping funnel, thermometer, gas inlet tube, $CaCl_2$-tube) is cooled in an ice bath to 5°C. The flask is flushed with nitrogen, then 128.5 g. of finely pulverized 87% by weight aqueous potassium hydroxide is added in portions, keeping the temperature below 20°C. After stirring at 20°C. for 1 hour, the brownish solution is cooled to 0° and 462 g. of 1-bromo-3,7-dimethyl-2,6-nonadiene is added dropwise over a period of 2 hours at 0°–2°C. After the addition, the suspension is stirred at 0°C. for 3 hours. The ice bath is then removed and stirring continued overnight. The reaction mixture is poured on a stirred mixture of 500 g. of ice, 500 ml. of 2N sodium hydroxide solution and 1.2 l of petrol ether (30° – 60°C.). After partitioning and separation, the aqueous layer is extracted twice with 400 ml. portions of petrol ether. The three petrol ether solutions are combined and washed successively with 1 l. of ice-water, twice with 500 ml. portions of cold 2N sodium hydroxide solution, 500 ml. of ice water and twice with 400 ml. portions of brine. The organic solution is dried ($Na_2SO_4$) and concentrated under reduced pressure to a volume of 900 ml. This solution is applied in the usual way on a column (diameter 13 cm) containing 1.5 kg. of Florisil (100–200 mesh, Fischer) in hexane-diethyl ether (99:1 parts by volume). Elution with 5 l. of hexane-diethyl ether (99:1 parts by volume) yields yellow oil, which is flash distilled to give 3,7-dimethyl-1-(3,4-methylenedioxy-phenoxy)-2,6-nonadiene as a colorless oil; b.p. 165°–170°C./0.025 mmHg.

Into a 2 l., four-necked flask (with stirrer, thermometer, CaCl$_2$-tube and stopper) is placed a solution of 162 g. of the 3,7-dimethyl-1-(3,4-methylenedioxyphenoxy)-2,6-nonadiene in 1.1 l. of methylene chloride. The flask is immersed in an ice-salt bath (−5°C.). When the vigorously stirred solution is cooled to 0°C., 125 g. of pulverized 85% m-chloroperbenzoic acid is added in ca 5 g. portions at such a rate to keep the reaction temperature at 1°–3° (2 hours). After complete addition, the white suspension is stirred for 2 hours, at 0°–1°C. The cold suspension is then poured on a mixture of 600 ml. of 2N sodium hydroxide solution and 300 g. of ice. After partitioning, the brown aqueous layer is extracted with two 250 ml. portions of methylene chloride. The combined organic solution is washed successively with three 250 ml. portions of cold 2N sodium hydroxide solution, 600 ml. of ice water and two 400 ml. portions of brine. The solution is dried (Na$_2$SO$_4$) and concentrated at reduced pressure to give 172 g. of a yellow oil. This crude epoxide is dissolved in 400 ml. of n-hexane-diethyl ether (10:1 parts by volume) and applied on a column (diameter 13 cm) containing 2 kg. of silica gel (E. Merck, AG 70-325 mesh) in n-hexane-diethyl ether (10:1 parts by volume). Elution (700 ml. cuts) with this mixture gives 6,7-epoxy-3,7-dimethyl-1-(3,4-methylenedioxyphenoxy)-2-nonene.

EXAMPLE 3

To a solution of 100 g. of 6,9,10-trimethyl-undeca-5,9-dien-2-one in 2,000 ml. of methylene chloride, there was added while cooling with ice, 100 g. of m-chloroperbenzoic acid. The resulting mixture was allowed to stand while constantly stirring at room temperature for 1 hour. The resulting mixture was diluted with 1,000 ml. of methylene chloride. The resulting solution was washed with ice-cold 1N sodium hydroxide solution and with a saturated sodium chloride solution, dried over sodium sulfate and evaporated. The residue was fractionally distilled under high vacuum. There was obtained 9,10-epoxy-6,9,10-trimethyl-undec-5-en-2-one; b.p. 89°–91°C./0.07 mmHg; $n_D^{20}$ = 1.4656.

To a solution of 25 g. of 9,10-epoxy-6,9,10-trimethyl-undec-5-en-2-one and 24.8 g. of diethyl phosphonoacetic acid ethyl ester in 160 ml. of absolute ethanol, there was added dropwise while cooling with ice, a solution containing 2.56 g. of sodium in 65 ml. of absolute ethyl alcohol. The mixture was allowed to stand for 14 hours at room temperature and evaporated subsequently under vacuum. The residue was poured into a standard aqueous sodium chloride solution, exhaustively extracted with diethyl ether, washed with a saturated aqueous sodium chloride solution, dried over sodium sulfate and evaporated. Fractional distillation at high vacuum gave 10,11-epoxy-3,7,10,11-tetramethyl-2,6-dodecadienoic acid ethyl ester; b.p. 110°–113°C./0.01 mmHg; $n_D^{20}$ = 1.4792.

EXAMPLE 4

Stabilized insecticide compositions, which comprise the juvenile hormone methyl 10,11-epoxy-7-ethyl-3,11-dimethyl-2,6-tridecadienoate (cis/trans mixture), a diluent (mixture containing xylene, a polyoxyethylated vegetable oil, and a monoglyceride of low molecular weight saturated coconut fatty acids), a mixture of NOGA and BHA as an anti-oxidant, and either an acrylonitrile U.V. absorber or a benzotriazole U.V. absorber, were formulated. A water emulsion of each composition containing 1% by weight of the juvenile hormone was prepared, and two milliliters samples were streaked over the surface of a glass plate (20 cm × 20 cm) so as to cover an entire surface of the plate. The water was allowed to evaporate from each plate, and the plates were then exposed to outdoor conditions from 8:30 a.m. to 5:00 p.m. Each night, samples were brought inside and stored at room temperature (about 22°C.). The outside temperature varied from 8°C. to 24°C. during the time of exposure. After two days exposure, samples were eluted with acetone and analyzed by gas chromatography and thin layer chromatography to determine the percent of the original juvenile hormone present in the exposed composition. The percent retention was calculated by the amount of juvenile hormone present in the exposed compositon divided by he original amount of juvenile hormone in the composition.

The results of this sample are summarized in Table 1.

Table 1

| | | | | | | | | | |
|---|---|---|---|---|---|---|---|---|---|
| Juvenile Hormone (Parts by Wt.) | 98 | 25 | 25 | 25 | 25 | 25 | 25 | 25 | 25 |
| Anti-oxidant (Parts by Wt.) | | | | | | | | | |
| NDGA | | 1 | 1 | 1 | 1 | 25 | 1 | 1 | 1 |
| BHA | | 1 | 1 | 1 | 1 | | 1 | 1 | 1 |
| Diluent (Parts by Wt.) | | 72 | 68 | 72 | 72 | 67.5 | 72 | 68 | 63 |
| Ultraviolet absorber (Parts by Wt.) | | | | | | | | | |
| 2-(2'-hydroxy-5'-methylphenyl)benzotriazole | 2 | 1 | 5 | | | | | | |
| 2-(3'-tert.butyl-2'-hydroxy-5'-methylphenyl)-5-chloro-benzotriazole | | | | 1 | | | | | |
| 2-(3',5'-ditert.butyl-2'-hydroxy-phenyl)-5-chloro-benzotriazole | | | | | 1 | | | | |
| Red Vet Petrolatum (a hydrocarbon solid, mp. about 40°C.) | | | | | | | 5 | | |
| 2-ethylhexyl-2-cyano-3,3-diphenyl acrylate | | | | | | | 1 | 5 | 10 |
| Percent Retention | 2–3 | 20 | 30 | 30–35 | 45 | 1–2 | 67 | 98 | 77 |

The results of this example show that percent retention of the juvenile hormone and, hence, its stability are substantially improved when an anti-oxidant is utilized in combination with an acrylenitrile U.V. absorber or a benzotriazole U.V. absorber, especially with an acrylonitrile U.V. absorber.

EXAMPLE 5

Utilizing the procedure of Example 4, percent retention of the juvenile hormone ethyl 10,11-epoxy-3,7,10,11-tetramethyl-2,6-dodecadienoate (cis/trans mixture), incorporated in a stabilized insecticide composition with a diluent (a mixture containing a polyoxyethylated vegetable oil and a monoglyceride of low molecular weight saturated coconut fatty acids), a mixture of NDGA and BHA as an anti-oxidant, and either a benzotriazole U.V. absorber or a benzophenone U.V. absorber, was determined after two days exposure.

The results of this example are summarized in Table 2.

Table 2

| | | | |
|---|---|---|---|
| Juvenile Hormone (Parts by Wt.) | 25 | 25 | 25 |
| Anti-oxidant (Parts by Wt.) | | | |
| NDGA | 1 | 1 | 1 |
| BHA | 1 | 1 | 1 |
| Diluent (Parts by Wt.) | 68 | 72 | 72 |
| Ultraviolet absorber (Parts by Wt.) | | | |
| 2-(2'-hydroxy-5'-methylphenyl)benzotriazole | 5 | | 1 |
| 2,2'-dihydroxy-4-methoxy-benzophenone | | 1 | |
| Percent Retention | 35 | 10 | 40–50 |

The results of this example show that percent retention of the juvenile hormone and, hence, its stability are substantially improved when the benzotriazole U.V. absorbers are utilized rather than a benzophenone U.V. absorber.

EXAMPLE 6

Utilizing the procedure of Example 4, with an outside temperature of about 21°C. to about 31°C., percent retention of the juvenile hormone 10,11-epoxy-3,7,11-trimethyl-1-(2-propynyloxy)-2,6-tridecadiene (cis/trans mixture), incorporated in a stabilized insecticide composition with a diluent (a mixture containing a polyoxyethylated vegetable oil, a monoglyceride of low molecular weight saturated coconut fatty acids and a saturated coconut base oil) and a selected U.V. absorber, was determined. Percent retention was measured after 1 and 2 days exposure.

The results of this example are summarized in Table 3.

Table 3

| | | | | | | |
|---|---|---|---|---|---|---|
| Juvenile Hormone (Parts by Wt.) | 50 | 50 | 50 | 50 | 50 | 50 |
| Diluent (Parts by Wt.) | 50 | 45 | 45 | 45 | 45 | 45 |
| U.V. absorber (Parts by Wt.) | | | | | | |
| 2-ethylhexyl-2-cyano-3,3-diphenyl acrylate | | 5 | | | | |
| ethyl-2-cyano-3,3-diphenyl acrylate | | | 5 | | | |
| p-octylphenyl-salicylate | | | | 5 | | |
| Resorcinol monobenzoate | | | | | 5 | |
| 4-dodecyloxy-2-hydroxy-benzophenone | | | | | | 5 |
| Percent Retention | | | | | | |
| 1 day | 5–10 | 50 | 40 | 10 | 10 | 20 |
| 2 days | 1–2 | 10–15 | 10–15 | 2 | 1–2 | 1–2 |

The results of this example demonstrate that comparing the ultraviolet absorbers selected from the group consisting of acrylonitriles, salicylates, benzoates, and benzophenones, only the acrylonitrile U.V. absorbers effectively improve the stability of juvenile hormones.

EXAMPLE 7

Utilizing the procedure of Example 6, percent retention of the juvenile hormone 6,7-epoxy-3,7-dimethyl-1-[3,4-(methylenedioxy)-phenoxy]-2-nonene (cis/trans mixture), incorporated in a stabilized insecticide composition with the acrylonitrile U.V. absorber 2-ethylhexyl-2-cyano-3,3-diphenyl acrylate and/or the phenolic anti-oxidant nordihydroguaiaretic acid and a diluent (a mixture containing xylene, acetone, a polyoxyethylated vegetable oil and a monoglyceride of low molecular weight saturated coconut fatty acids), was determined. Percent retention was measured after one and two days exposure. The results of this example are summarized in Table 4.

Table 4

| | | | | | | | |
|---|---|---|---|---|---|---|---|
| Juvenile Hormone (Parts by Wt.) | 50 | 50 | 50 | 50 | 50 | 50 | 50 |
| U.V. absorber (Parts by Wt.) | | 5 | 5 | 10 | 10 | 10 | |
| Anti-oxidant (Parts by Wt.) | | 2.5 | | 2.5 | | 2.5 | |
| Diluent (Parts by Wt.) | 50 | 42.5 | 45 | 37.5 | 40 | 37.5 | 50 |
| Percent Retention | | | | | | | |
| 1 day | 20–25 | 40–45 | 65–75 | 35–40 | 50–60 | 50 | 5–10 |
| 2 days | 5–10 | 15–20 | 35–50 | 30 | 50 | 25 | 4–5 |

The results of this example demonstrate that the stability of juvenile hormones is substantially increased by adding thereto an acrylonitrile U.V. absorber and a phenolic anti-oxidant.

The results of this example of further demonstrate that with juvenile hormones of formula III, above, the acrylonitrile U.V. absorber is remarkably effective, by itself, for improving the stability of these juvenile hormones, particularly in concentrations of 5 to 10% weight percent.

EXAMPLE 8

Utilizing the procedure of Example 7, percent retention of the juvenile hormones 6,7-epoxy-1-(p-ethylphenoxy)-3,7-dimethyl-2-octene (cis/trans mixture), and 10,11-epoxy-3,7,11-trimethyl-1-(2-propynyloxy)2,6-tridecadiene (cis/trans mixture), incorporated in a stabilized insecticide composition with, as a phenolic anti-oxidant, the mixture of NDGA and BHA, the acrylonitrile U.V. absorber, 2-ethylhexyl-2-cyano-3,3-diphenyl acrylate, and a diluent (a mixture containing a polyoxyethylated vegetable oil, a monoglyceride of low molecular weight saturated coconut fatty acids and a saturated coconut base oil), was determined after one and two days exposure.

The results of this example are summarized in Table 5.

EXAMPLE 9

Stabilized insecticide compositions, which comprise the juvenile hormone methyl 10,11-epoxy-7-ethyl-3,11-dimethyl-2,6-tridecadienoate (cis/trans mixture), a diluent (mixture containing a polyoxyethylated vegetable oil and a monoglyceride of lower molecular weight saturated coconut fatty acid), an anti-oxidant and selected U.V. absorbers, were formulated. A water emulsion of each composition containing 1% of the juvenile hormone was applied outdoors to rhododendron leaves at a level of 2 mg. active compound/leaf. The leaves were covered with plastic bags overnight to prevent rain wash-off and the leaves remained on the plant until sampling time. The outdoor temperature varied from about 8°C. to 24°C. during the experiment. The samples were exposed for two or three days and percent retention was measured. Analysis of the samples was carried out as in Example 4. The symbol "—" indicates that percent retention was not determined.

The results of this example are summarized in Table 6.

Table 6

| Juvenile Hormone (Parts by Wt.) | 25 | 25 | 25 | 25 | 25 |
|---|---|---|---|---|---|
| Anti-oxidant (Parts by Wt.) | | | | | |
| NDGA | 1 | 1 | 1 | 1 | 1 |
| BHA | 1 | 1 | 1 | 1 | 1 |
| U.V. absorber (Parts by Wt.) | | | | | |
| 2,2'-dihydroxy-4-methoxy-benzophenone | 1 | | | | |
| 2-(3',5'-ditert.butyl-2'-hydroxyphenyl)-5-chloro-benzotriazole | | 1 | | | |
| 2-ethylhexyl-2-cyano-3,3-diphenyl acrylate | | | 1 | 5 | 10 |
| Diluent (Parts by Wt.) | 72 | 72 | 72 | 68 | 63 |
| % Retention | | | | | |
| 2 days | 42 | 56 | — | — | — |
| 3 days | 0 | — | 36 | 39 | 34 |

The results of this example demonstrate that the stability of juvenile hormones is substantially increased after two days exposure to air and sunlight by the use of Table 5

| Juvenile Hormone (Parts by Wt.) | | | | | | |
|---|---|---|---|---|---|---|
| 6,7-epoxy-1-(p-ethylphenoxy)-3,7-dimethyl-2-octene | 50 | 50 | 50 | 50 | | |
| 10,11-epoxy-3,7,11-trimethyl-1-(2-propynyloxy)-2,6-tridecadiene | | | | | 50 | 50 |
| U.V. absorber (Parts by Wt.) | | 5 | | 5 | | 5 |
| Anti-oxidant (Parts by Wt.) | | | | | | |
| NDGA | | | 1.25 | 1.25 | | 1.25 |
| BHA | | | 1.25 | 1.25 | | 1.25 |
| Diluent (Parts by Wt.) | 50 | 45 | 47.5 | 42.5 | 50 | 42.5 |
| Percent Retention | | | | | | |
| 1 day | 35 | 55 | 60–65 | 70–75 | 15–20 | 35–40 |
| 2 days | 5 | 10 | 10–20 | 20–25 | 1–2 | 15 |

The results of this example demonstrate that the stability of juvenile hormones can be substantially improved against degradation by the synergistic effect of both a phenolic anti-oxidant and an acrylonitrile U.V. absorber.

a phenolic anti-oxidant and either a benzotriazole U.V. absorber or an acrylonitrile U.V. absorber, especially an acrylonitrile U.V. absorber. The example also demonstrates that an acrylonitrile U.V. absorber is particularly valuable in concentration of 1 to 10 weight percent.

I claim:

1. A stabilized insecticide composition comprising;
  a. from about 10 to 75 weight percent of a juvenile hormone of the formula:

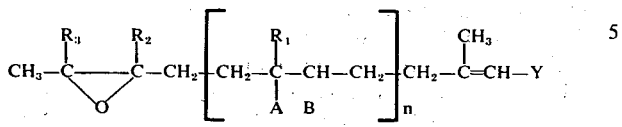

wherein Y is —COOR$_4$, —CH$_2$—O—C≡CH,

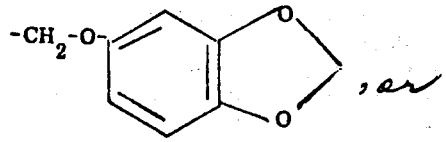

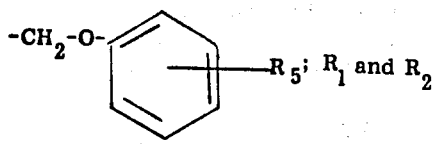

are hydrogen, methyl or ethyl; R$_3$ is methyl or ethyl; R$_4$ and R$_5$ are hydrogen or lower alkyl; n is an integer of from 0 to 1; and A and B are hydrogen or are taken together to form a carbon to carbon bond;
  b. from about 1% to 25% by weight of a phenolic anti-oxidant; and
  c. from about 1 to 20% by weight of an acrylonitrile u.v. absorber selected from the group consisting of ethyl-2-cyano-3,3-diphenyl acrylate and 2-ethylhexyl-2-cyano-3,3-diphenyl acrylate.

2. The stabilized insecticide composition of claim 1 comprising 25 to 50 weight percent of the juvenile hormone.

3. The stabilized insecticide composition of claim 1 comprising 5 to 10 weight percent u.v. absorber.

4. The stabilized insecticide composition of claim 1 wherein said phenolic anti-oxidant is substituted with hydroxy, lower alkyl or lower alkoxy.

5. The composition of claim 1 wherein said juvenile hormone agent is 10,11-epoxy-3,7,11-trimethyl-1-(2-propynyloxy)-2,6-tridecadiene.

6. The composition of claim 1 wherein said juvenile hormone agent is 6,7-epoxy-1-(p-ethylphenoxy)-3,7-dimethyl-2-octene.

7. A concentrate composition comprising from about 10 to 80% by weight of a stabilized insecticide composition containing:
  a. from about 10 to 75 weight percent of a juvenile hormone of the formula:

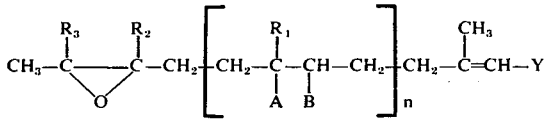

wherein Y is —COOR$_4$, —CH$_2$—O—CH$_2$—C≡CH,

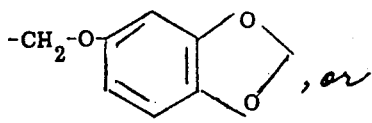

R$_3$ hydrogen methyl or ethyl; R$_4$ and R$_5$ are hydrogen or lower alkyl; n is an integer of from 0 to 1; and A and B are hydrogen or are taken together to form a carbon to carbon bond;
  b. from about 1% to 25% by weight of a phenolic anti-oxidant, and;
  c. from about 1 to 20% by weight of an acrylonitrile u.v. absorber selected from the group consisting of ethyl-2-cyano-3,3-diphenyl acrylate and 2-ethylhexyl-2-cyano-3,3-dimethyl acrylate and from about 20% to 90% by weight of an inert carrier material.

8. The concentrate composition of claim 7 wherein said juvenile hormone is 6,7-epoxy-3,7-dimethyl-1-[3,4-(methylenedioxy)-phenoxy]-2-nonene.

9. The concentrate composition of claim 7 wherein said stabilized insecticide composition includes 25 to 50 weight percent of the juvenile hormone and 5 to 10 weight percent of u.v. absorber.

10. A ready to use pest control agent comprising from about 0.01 to 20% by weight of a stabilized insecticide composition containing
  a. from about 10 to 75 weight percent of a juvenile hormone of the formula:

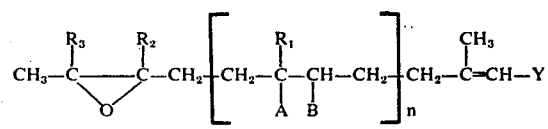

wherein Y is —COOR$_4$, —CH$_2$—O—CH$_2$—C≡CH,

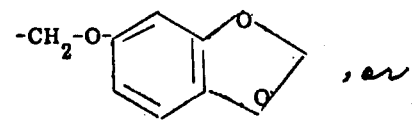

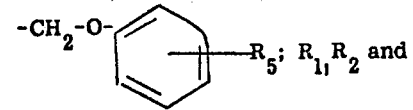

R$_3$ is hydrogen, methyl or ethyl; R$_4$ and R$_5$ are hydrogen or lower alkyl; n is an integer of from 0 to 1; and A and B are hydrogen or are taken together to form a carbon to carbon bond;
  b. from about 1% to 25% by weight of a phenolic anti-oxidant; and
  c. from about 1 to 20% by weight of an acrylonitrile u.v. absorber selected from the group consisting of ethyl-2-cyano-3,3-diphenyl acrylate and 2-ethylhexyl-2-cyano-3,3-diphenyl acrylate and from about 80% to 99.9% by weight of an inert carrier material.

11. The ready-to-use pest-control agent of claim 10 wherein said stabilized insecticide composition includes 25 to 50 weight percent of the juvenile hormone and 5 to 10 weight percent of u.v. absorber.

12. The ready-to-use pest-control agent of claim 10 comprising 0.1–10 weight percent of the stabilized insecticide composition and 99.9 to 90 weight percent of the inert carrier material.

* * * * *